(12) United States Patent
Line et al.

(10) Patent No.: US 10,933,821 B2
(45) Date of Patent: Mar. 2, 2021

(54) SEATING ASSEMBLY FOR A VEHICLE WITH EMITTERS OF ULTRAVIOLET C RADIATION TO DISINFECT SEATBELT WEBBING

(71) Applicant: Ford Global Technologies, LLC, Dearborn, MI (US)

(72) Inventors: Johnathan Andrew Line, Northville, MI (US); Daniel Ferretti, Commerce Township, MI (US); Michael Kolich, Windsor (CA); Scott Holmes Dunham, Redford, MI (US); Edward Joseph DeSmet, Canton, MI (US); Benjamin Yilma, Canton, MI (US); Matthew Anthony Majkowski, Dearborn, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 4 days.

(21) Appl. No.: 16/367,915

(22) Filed: Mar. 28, 2019

(65) Prior Publication Data

US 2020/0307472 A1   Oct. 1, 2020

(51) Int. Cl.
| | |
|---|---|
| *B60R 15/00* | (2006.01) |
| *A61L 2/10* | (2006.01) |
| *B60R 22/34* | (2006.01) |
| *B60R 22/26* | (2006.01) |

(52) U.S. Cl.
CPC ............. *B60R 15/00* (2013.01); *A61L 2/10* (2013.01); *A61L 2202/11* (2013.01); *B60R 22/26* (2013.01); *B60R 22/34* (2013.01); *B60R 2022/3402* (2013.01)

(58) Field of Classification Search
None
See application file for complete search history.

(56) References Cited

U.S. PATENT DOCUMENTS

| | | | |
|---|---|---|---|
| 5,129,129 A * | 7/1992 | Collins ............. | A44B 11/2576 24/579.11 |
| 5,385,584 A * | 1/1995 | Teramura ................. | D06B 3/18 68/5 D |
| 9,592,312 B2 | 3/2017 | Lyslo et al. | |
| 10,376,605 B1 | 8/2019 | Majdali et al. | |

(Continued)

FOREIGN PATENT DOCUMENTS

| | | |
|---|---|---|
| CN | 2726973 Y | 9/2005 |
| DE | 102018002328 A1 | 9/2019 |
| EP | 26678964 A1 | 12/2013 |

*Primary Examiner* — Drew J Brown
(74) *Attorney, Agent, or Firm* — David Coppiellie; Price Heneveld LLP

(57) ABSTRACT

A seating assembly for a vehicle comprising: a seat; a seatback including an occupant side configured to contact and support an occupant of the seating assembly, a rear side that faces in the generally opposite direction as the occupant side, and a top portion; seatbelt webbing, the seatbelt webbing extending along the rear side of the seatback; a plurality of emitters of UVC radiation; and an emitter support structure attached to the seatback that supports the plurality of emitters of UVC radiation such that the plurality of emitters of UVC radiation emit UVC radiation onto the seatbelt webbing extending along the rear side of the seatback.

20 Claims, 14 Drawing Sheets

(56) References Cited

U.S. PATENT DOCUMENTS

| | | | |
|---|---|---|---|
| 2003/0053929 A1* | 3/2003 | Walker | A01N 33/12 |
| | | | 422/28 |
| 2007/0053188 A1 | 3/2007 | New et al. | |
| 2007/0207066 A1 | 9/2007 | Thur et al. | |
| 2008/0175761 A1 | 7/2008 | Thur et al. | |
| 2016/0000951 A1 | 1/2016 | Kreiner et al. | |
| 2016/0089459 A1 | 3/2016 | Boodaghians et al. | |
| 2016/0250362 A1 | 9/2016 | Mackin | |
| 2017/0096120 A1* | 4/2017 | Marew | B60R 22/12 |
| 2017/0313278 A1 | 11/2017 | Marew | |
| 2018/0229694 A1* | 8/2018 | Salter | B08B 7/0035 |
| 2019/0382597 A1* | 12/2019 | Gross | C09D 7/61 |
| 2020/0061223 A1* | 2/2020 | Hallack | A61L 2/084 |

* cited by examiner

SEATING ASSEMBLY FOR A VEHICLE WITH EMITTERS OF ULTRAVIOLET C RADIATION TO DISINFECT SEATBELT WEBBING

FIELD OF THE INVENTION

The present invention generally relates to a seating assembly for a vehicle, and more particularly, to a seating assembly for a vehicle with emitters of ultraviolet C ("UVC") radiation to disinfect seatbelt webbing.

BACKGROUND OF THE INVENTION

Seatbelt webbing used in vehicles harbor potentially health-deteriorating bacteria and other microorganisms. That problem is especially prevalent in vehicles used in connection with peer-to-peer ridesharing services and taxicab services. The problem is also prevalent in vehicles used in mass and public transportation.

SUMMARY OF THE INVENTION

According to a first aspect of the present invention, a vehicle comprises: one or more emitters of ultraviolet C (UVC) radiation positioned to emit UVC radiation onto seatbelt webbing of a vehicle.

Embodiments of the first aspect of the invention can include any one or a combination of the following features:
  seatbelt webbing including a length, which includes a wound portion and an unwound portion;
  a retractor including a housing rotatably supporting a shaft, around which the wound portion of the length of the seatbelt webbing is wound, the unwound portion of the seatbelt webbing extending away from the housing;
  at least one of the one or more emitters of the UVC radiation is operably coupled to the housing and positioned to emit UVC radiation onto the seatbelt webbing;
  the seatbelt webbing includes a length having an unwound portion, a first primary surface, a second primary surface that faces in an opposite direction as the first primary surface, a first edge, and a second edge, the first primary surface and the second primary surface extending laterally from the first edge to the second edge and lengthwise along the length of the seatbelt webbing;
  at least an exposed portion of the first primary surface of the wound portion of the seatbelt webbing is exposed within the housing;
  the at least one of the emitters of the UVC radiation is positioned to emit UVC radiation onto the exposed portion of the first primary surface of the wound portion of the seatbelt webbing;
  an emitter support structure including: a first surface facing the first primary surface of the seatbelt webbing, the emitter support structure supporting the at least one of the emitters of the UVC radiation between the first surface and the first primary surface of the seatbelt webbing;
  an attachment portion attached to the housing of the retractor, the attachment portion supporting the at least one of the emitters of the UVC radiation positioned to emit UVC radiation onto the exposed portion of the first primary surface of the wound portion of the seatbelt webbing;
  an extension portion extending away from the attachment portion and the retractor, the extension portion supporting one or more of the emitters of the UVC radiation positioned to emit UVC radiation onto the first primary surface of the seatbelt webbing at the unwound portion of the seatbelt webbing;
  the emitter support structure supports the one or more emitters of UVC radiation between the first primary surface of the seatbelt webbing and the first surface of the emitter support structure such that UVC radiation is emitted along at least a portion of the unwound portion of the length of the seatbelt webbing;
  the emitter support structure further including a second surface facing the second primary surface of the seatbelt webbing, the emitter support structure supporting at least one of the emitters of UVC radiation between the second primary surface of the seatbelt webbing and the second surface of the emitter support structure such that UVC radiation is emitted along at least a portion of the unwound portion of the seatbelt webbing;
  each of the emitters of UVC radiation is a cutout into a light pipe, which transmits UVC radiation, such that UVC radiation transmits through the light pipe, through the cutout, and onto the seatbelt webbing;
  the first surface of the emitter support structure reflects UVC radiation;
  the emitter support structure surrounds at least a portion of the unwound portion of the length of the seatbelt webbing;
  the emitter support structure comprising a first housing portion providing the first surface and a second housing portion providing the second surface and coupled to the first housing portion such that the first housing portion and the second housing portion together form a lengthwise chamber that houses at least a portion of the unwound portion of the length of the seatbelt webbing, and UVC radiation is emitted within the chamber;
  a floor portion;
  a seating assembly including a seat including a bottom portion that generally faces the floor portion;
  the seating assembly further including a seatback including an occupant side that is configured to contact and support an occupant of the seating assembly, a rear side that generally faces rearward from the perspective of the occupant, and a top portion that is furthest away from the floor portion of the vehicle;
  a retractor disposed between the floor portion of the vehicle and the bottom portion of the seat, the retractor including a housing rotatably supporting a shaft;
  seatbelt webbing including a length, which includes a wound portion wound around the shaft of the retractor, and an unwound portion;
  the unwound portion extends rearward away from the housing, then upwards generally parallel to the rear side of the seatback, then over the top portion of the seatback, and then at least partially downwards generally parallel to the forward side of the seatback;
  the one or more emitters of UVC radiation include a plurality of emitters of UVC radiation positioned adjacent the seatbelt webbing to emit UVC radiation onto the seatbelt webbing where the unwound portion of the seatbelt webbing extends upwards generally parallel to the rear side of the seatback;
  an emitter support structure that forms a chamber that surrounds the unwound portion of the seatbelt webbing that extends upwards generally parallel to the rear side of the seatback and structurally supports the plurality of emitters of UVC radiation within the chamber;

the seatbelt webbing including a first primary surface, a second primary surface that faces in an opposite direction as the first primary surface, a first edge, and a second edge, the first primary surface and the second primary surface extending laterally from the first edge to the second edge and lengthwise along the length of the seatbelt webbing;

the plurality of emitters of UVC radiation positioned to emit UVC radiation onto the first primary surface and the second primary surface of the seatbelt webbing;

the emitter support structure including a parabolic reflective surface cooperating with each of the plurality of emitters of UVC radiation and disposed opposing the first edge or the second edge, or both, of the seatbelt webbing, each parabolic reflective surface has a focal point, and each of the plurality of emitters of UVC radiation is positioned between the parabolic reflective surface and the focal point.

According to a second aspect of the present invention, a seating assembly for a vehicle comprises: a seat; a seatback including an occupant side configured to contact and support an occupant of the seating assembly, a rear side that faces in the generally opposite direction as the occupant side, and a top portion; seatbelt webbing, the seatbelt webbing extending along the rear side of the seatback; a plurality of emitters of UVC radiation; and an emitter support structure attached to the seatback that supports the plurality of emitters of UVC radiation such that the plurality of emitters of UVC radiation emit UVC radiation onto the seatbelt webbing extending along the rear side of the seatback.

Embodiments of the second aspect of the invention can include any one or a combination of the following features:

the emitter support structure forms a chamber that surrounds at least a portion of the seatbelt webbing but allows the seatbelt webbing to move through the chamber, the emitter support structure supporting the plurality of emitters of UVC radiation to emit UVC radiation within the chamber;

a frame providing structural support for the seat;

a retractor attached to the frame, the seatbelt webbing able to retract into and extract out of the retractor;

the seatbelt webbing extends from the retractor then along the rear side of the seatback toward the top portion; and the emitter support structure at least partially encases the retractor, and the chamber extends continuously from the retractor, alongside the rear side of the seatback, and terminating at or near the top portion of the seatback.

According to a third aspect of the present invention, an emitter support structure for a seating assembly of a vehicle comprises: a housing forming a chamber and having fastening features configured to permit fastening of the emitter support structure to the seating assembly; and a plurality of emitters of UVC radiation supported by the housing and emitting UVC radiation into the chamber.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 1:
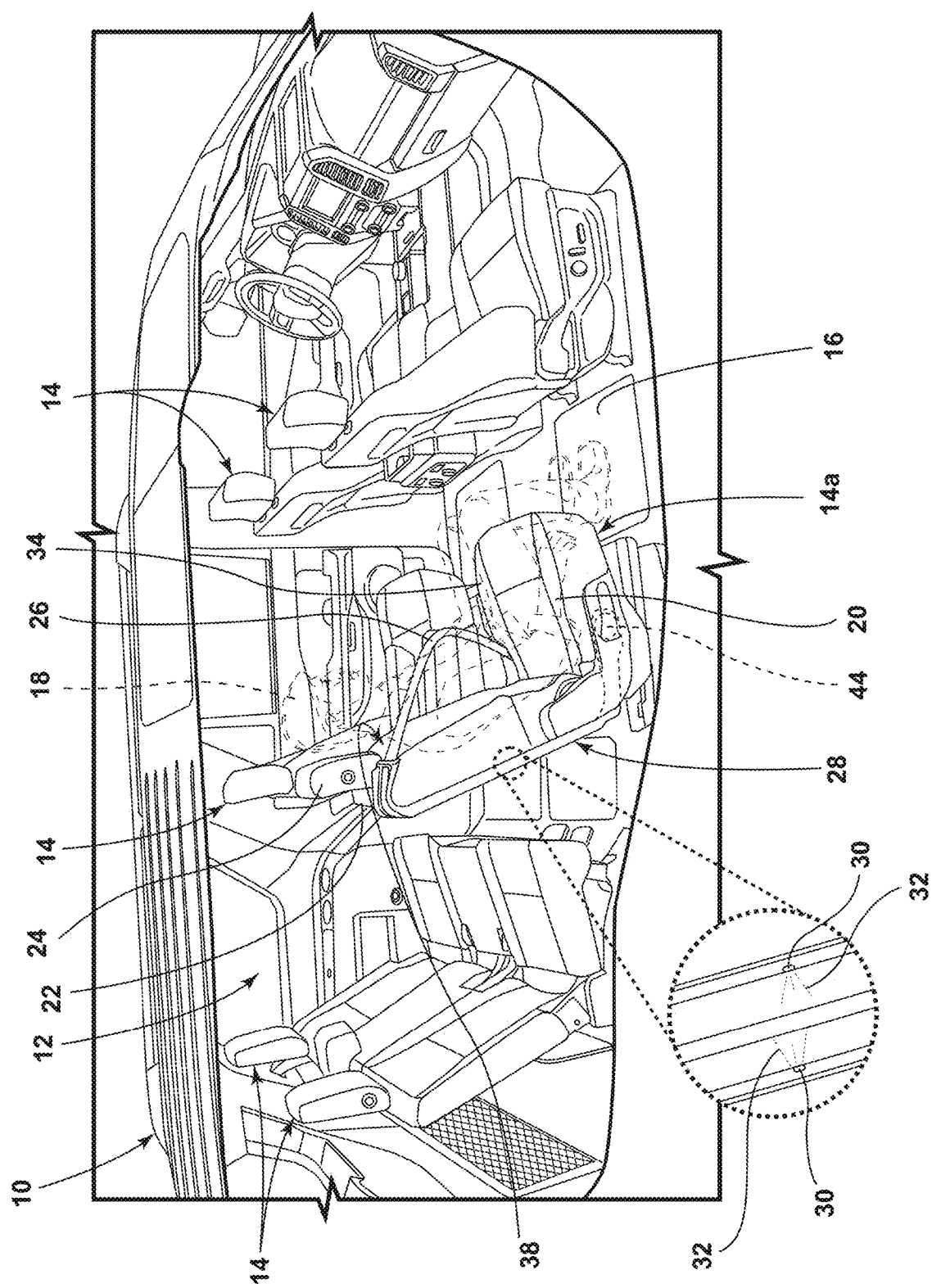
FIG. 1 is a perspective view of a vehicle, with a cutaway view into an interior of the vehicle, illustrating a seating assembly including seatbelt webbing and an emitter support structure that supports emitters of UVC radiation that radiate UVC radiation onto the seatbelt webbing.

For purposes of description herein, the terms "top," "bottom," "rear," "rearward," "forward," "downwards," "upwards," and derivatives thereof, shall relate to the invention as oriented in FIG. 1. However, it is to be understood that the invention may assume various alternative orientations, except where expressly specified to the contrary. It is also to be understood that the specific devices and processes illustrated in the attached drawing, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to FIG. 1, a vehicle 10 includes an interior 12. The vehicle 10 further includes one or more seating assemblies 14 and a floor portion 16 supporting the one or more seating assemblies 14, such as a seating assembly 14a. Although the present disclosure focuses upon the seating assembly 14a, it should be understood that the description of the seating assembly 14a applies equally to all the seating assemblies 14. The seating assembly 14a is configured to support an occupant 18 and, as such, includes a seat 20, a seatback 22, and a head restraint 24. Other designs are possible for the seating assembly 14a to support the occupant 18, such as not including the head restraint 24, without departing from the disclosure. The vehicle 10 further includes seatbelt webbing 26 cooperating with the seating assembly 14a to keep the occupant 18 seated upon the seating assembly 14a. The vehicle 10 further includes an emitter support structure 28 attached to the seating assembly 14a, which emitter support structure 28, as discussed further below supports at least one emitter 30 of ultraviolet C ("UVC") radiation 32, such as a plurality of emitters 30 of the UVC radiation 32. The UVC radiation 32 is electromagnetic radiation having a wavelength between 100 nm and 280 nm. The emitters 30 of the UVC radiation 32 are positioned to emit the UVC radiation 32 onto the seatbelt webbing 26. The UVC radiation 32 has a germicidal effect, destroying microorganisms present on the seatbelt webbing 26. The portion of the seatbelt webbing 26 that is subjected to the UVC radiation 32 harbors less potentially health-deteriorating bacteria and other microorganisms than before being so subjected. The vehicle 10 can be a car, truck, sports utility vehicle, van, bus, airplane, or passenger car used in rail transport, among other things.

Figure 2:
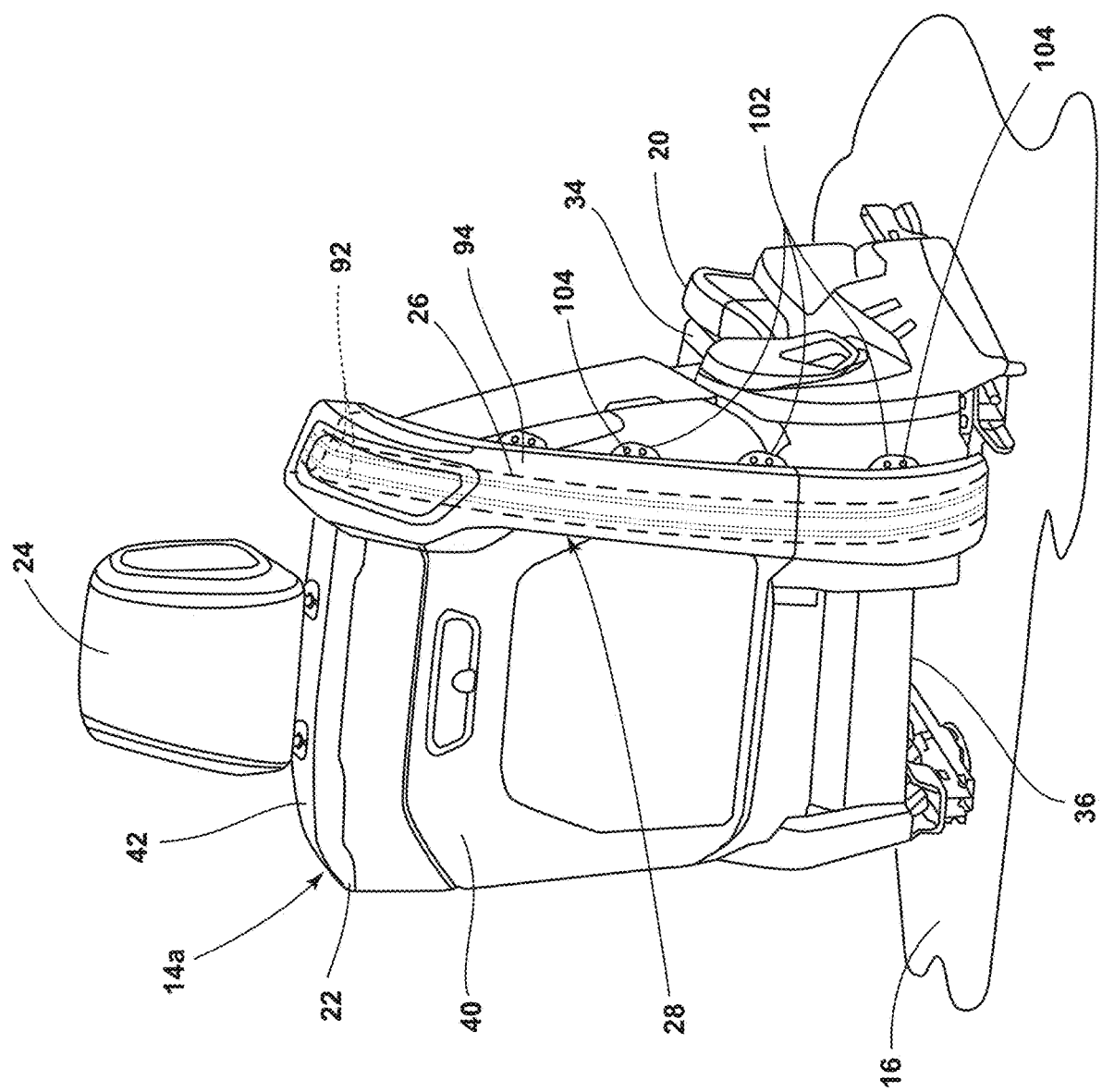
FIG. 2 is a rear perspective view of the seating assembly of FIG. 1, illustrating the seating assembly including a seatback and the emitter support structure extending alongside a rear part of the seatback to a top portion of the seatback.
Figure 3:
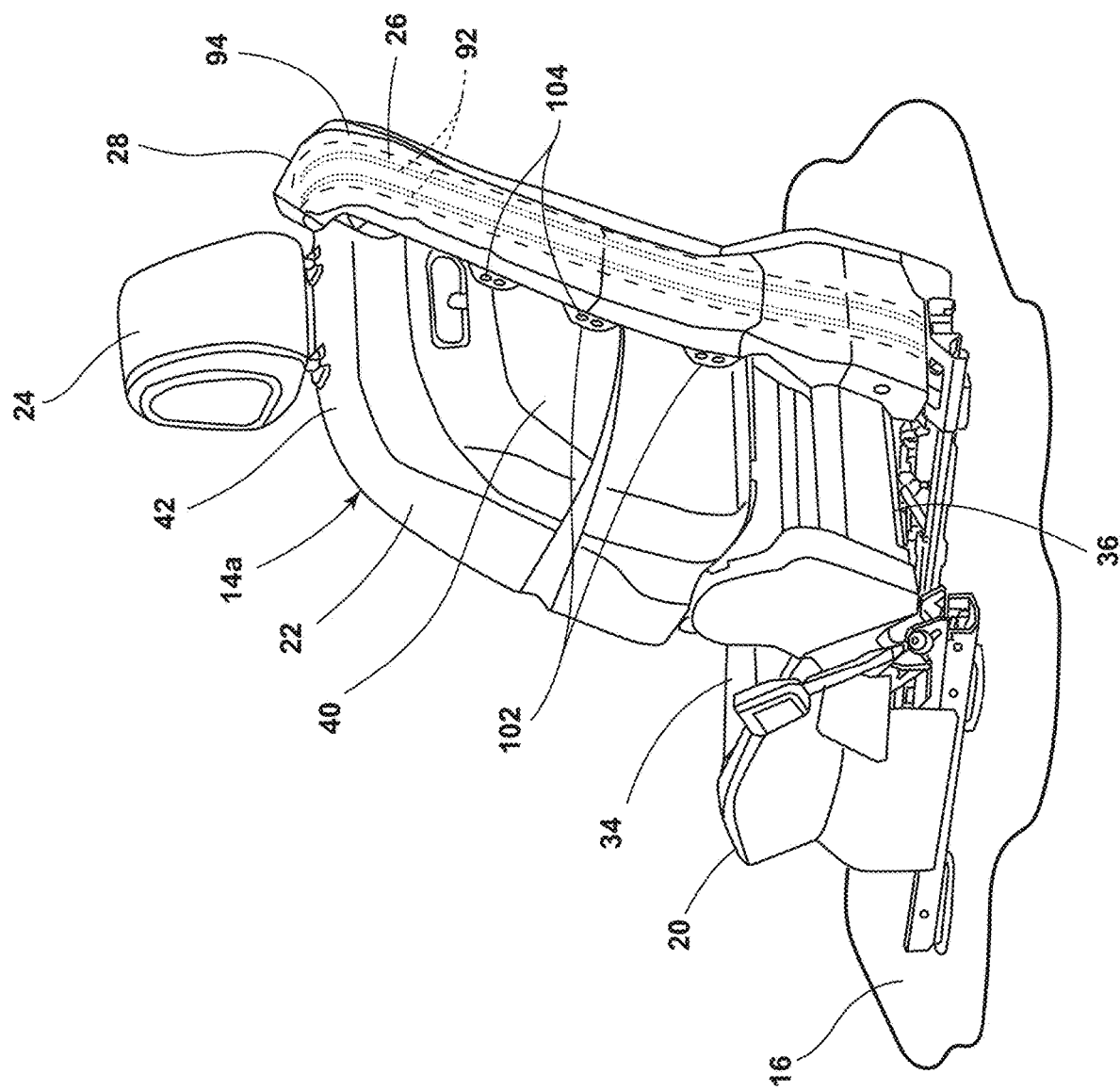
FIG. 3 is a rear perspective view of the seating assembly of FIG. 1, illustrating the seating assembly including a seat and the emitter support structure extends from the rear part of the seatback to a bottom portion of the seat, between a floor portion of the vehicle and the bottom portion of the seat.

Referring now additionally to FIGS. 2 and 3, the seat 20 of the seating assembly 14a includes a top portion 34 and a bottom portion 36. The top portion 34 contacts and supports the occupant 18 when the occupant 18 occupies the seating assembly 14a. The bottom portion 36 generally faces the floor portion 16 of the vehicle 10. Similarly, the seatback 22 includes an occupant side 38, a rear side 40, and a top portion 42. The occupant side 38 contacts and supports the occupant 18 when the occupant 18 occupies the seating assembly 14a. The rear side 40 generally faces in the opposite direction as the occupant side 38 and thus faces rearward from the perspective of the occupant 18. In the illustrated embodiment, the occupant side 38 faces forward and the rear side 40 faces rearward from the perspective of the vehicle 10. In other embodiments, the seating assembly 14a can face in any direction relative to the vehicle 10. The top portion 42 of the seatback 22 is the portion of the seatback 22 furthest away from the floor portion 16 of the vehicle 10. In the illustrated embodiment, the head restraint 24 extends from the top portion 42 of the seatback 22.

Figure 4:
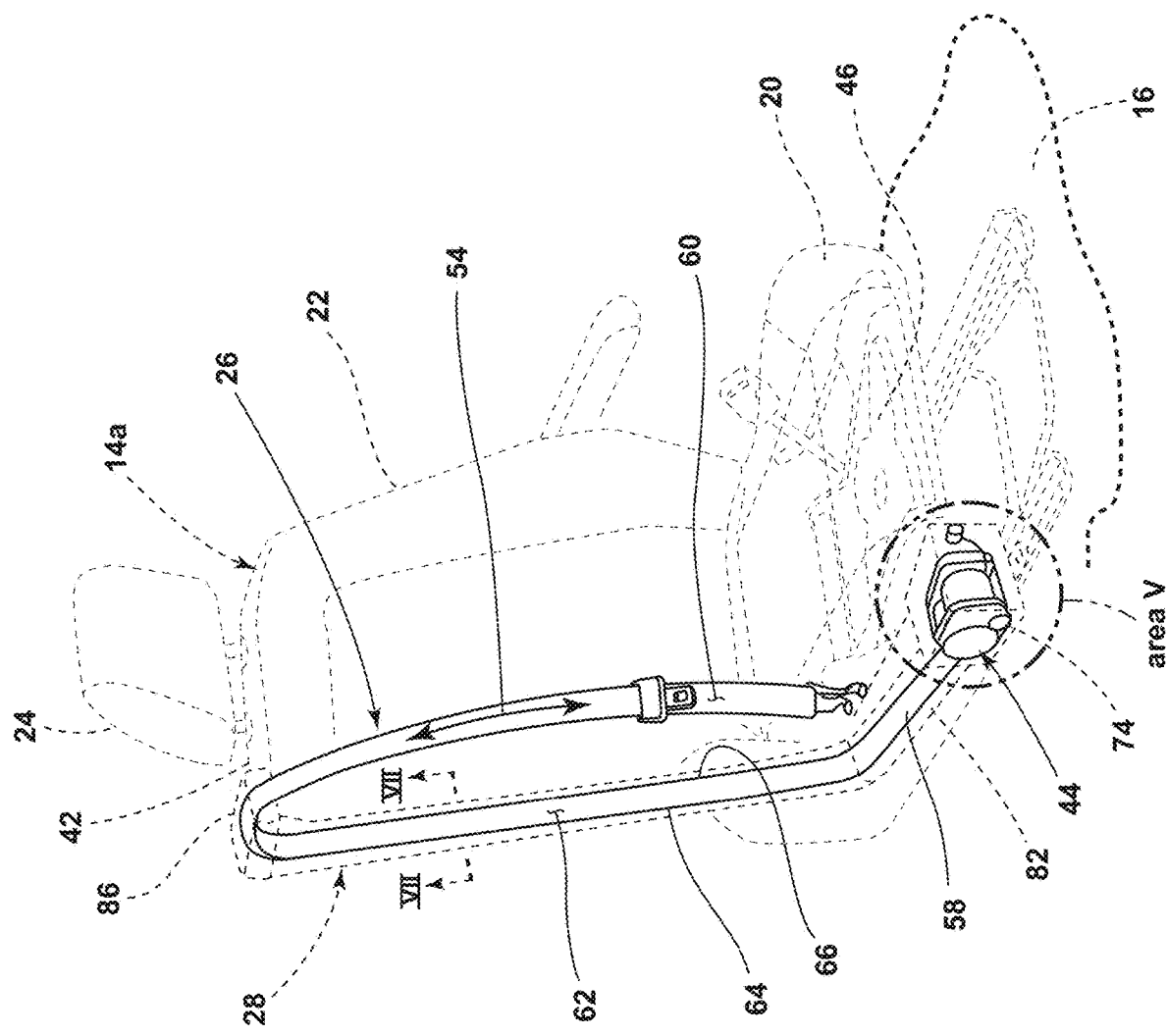
FIG. 4 is a front perspective view of the seating assembly of FIG. 1, with most of the seating assembly in phantom except for the seatbelt webbing, a frame of the seat, and a retractor attached to the frame that retracts the seatbelt webbing or from which the seatbelt webbing extracts.

Referring now additionally to FIG. 4, the vehicle 10 further includes a retractor 44 for the seatbelt webbing 26. The seating assembly 14a includes a frame 46. The frame 46 provides structural support for the seat 20 and, optionally, the seatback 22. In the illustrated embodiment, the retractor 44 is attached to the frame 46, and is disposed between the floor portion 16 of the vehicle 10 and the bottom portion 36 of the seat 20. However, the retractor 44 could be attached elsewhere within the vehicle 10 without departing from the disclosure. Attaching the retractor 44 to the frame 46 or some other aspect of the seating assembly 14a allows the retractor 44 to move as the seating assembly 14a moves, such as forward or rearward relative to the floor portion 16. Except for the features described herein, the retractor 44 can be any retractor typically used for the seatbelt webbing 26, where the seatbelt webbing 26 is able to retract into and extract out of the retractor 44.

Figure 5:
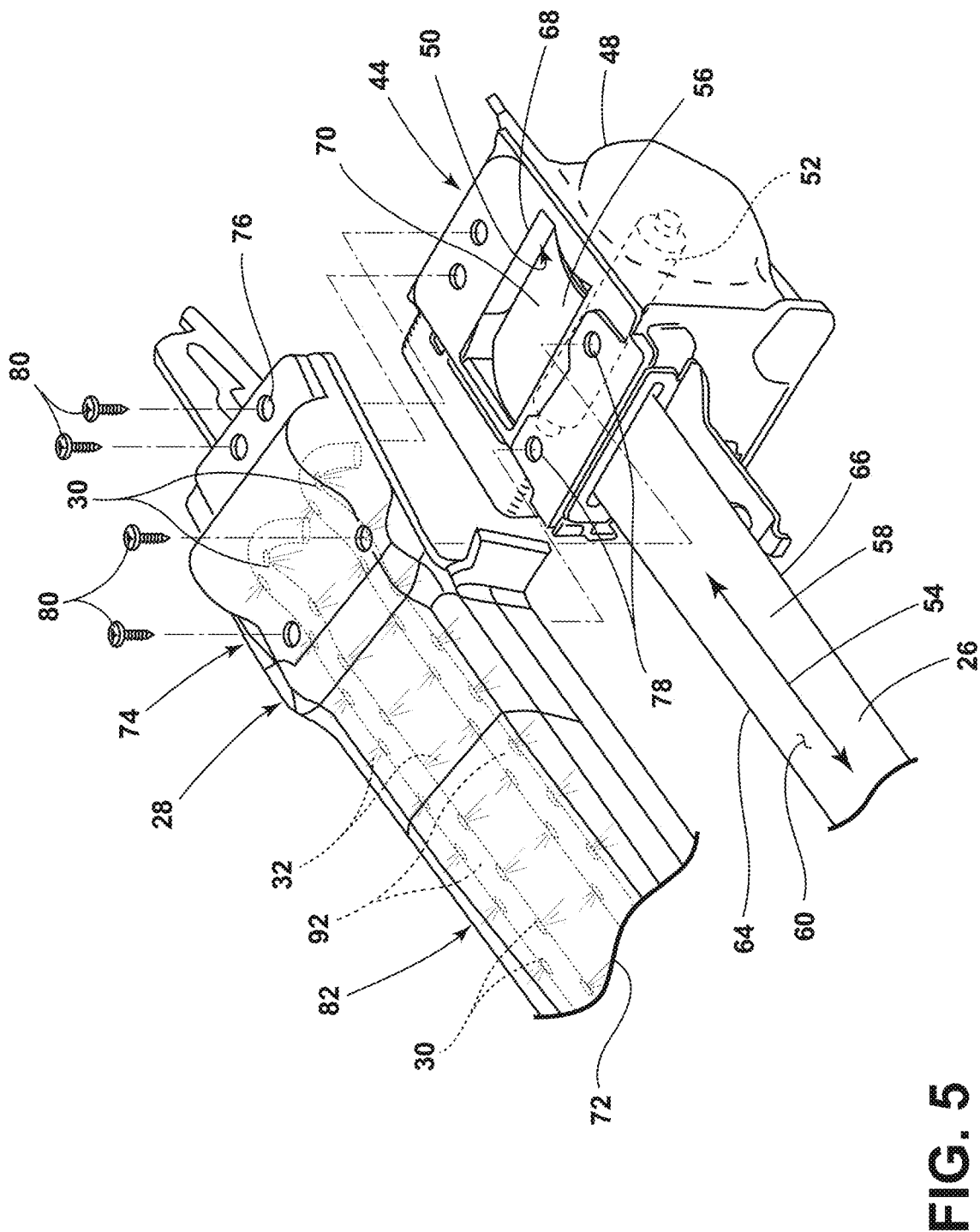
FIG. 5 is an underside perspective view of area V of FIG. 4, illustrating, in exploded view, an attachment portion of the emitter support structure attached to a housing of the retractor such that emitters of UVC radiation are positioned to emit UVC radiation onto an exposed portion of a wound portion of the seatbelt webbing through a window in the housing of the retractor.

Referring now additionally to FIG. 5, the retractor 44 includes a housing 48 and an interior 50 within and defined by the housing 48. The housing 48 rotatably supports a shaft 52 within the interior 50. The seatbelt webbing 26 has a length 54, which extends from the interior 50 of the housing 48 and over the seatback 22, as will be further explained. The length 54 includes a wound portion 56 and an unwound portion 58. The wound portion 56 of the seatbelt webbing 26 is wound within the interior 50 of the retractor 44, more specifically around the shaft 52. The unwound portion 58 is not so wound and extends away from the housing 48. The seatbelt webbing 26 further includes a first primary surface 60 and a second primary surface 62. The secondary primary surface 62 faces in an opposite direction as the first primary surface 60. The seatbelt webbing 26 further includes a first edge 64 and a second edge 66. The first edge 64 and the second edge 66 are on opposite sides of the seatbelt webbing 26. The first primary surface 60 and the second primary surface 62 each extend laterally from the first edge 64 to the second edge 66, and lengthwise along the length 54 of the seatbelt webbing 26. In some embodiments of the housing 48, like the illustrated embodiment, the housing 48 of the retractor 44 includes a window 68 into the interior 50. In such an embodiment, at least an exposed portion 70 of the seatbelt webbing 26 is exposed within the housing 48 through the window 68, such as the exposed portion 70 of the first primary surface 60 of the wound portion 56.

The emitter support structure 28 includes a first surface 72. The first surface 72 faces the first primary surface 60 of the seatbelt webbing 26. At least one of, or a portion of, the plurality of emitters 30 of the UVC radiation 32 are disposed at the first surface 72, such that the emitters 30 of the UVC radiation 32 are supported between the first surface 72 and the first primary surface 60 of the seatbelt webbing 26.

In the illustrated embodiment, the emitter support structure 28 includes an attachment portion 74. The attachment portion 74 is attached to the housing 48 of the retractor 44. For example, the attachment portion 74 and the housing 48 each include cooperating fastener receivers 76, 78, respectively, to receive fasteners 80 that fasten the attachment portion 74 to the housing 48. Instead of the fasteners 80 and the fastener receivers 76, 78, the attachment portion 74 and the housing 48 can each include cooperating snap-fit fastening features (not illustrated). When attached, the attachment portion 74 faces the window 68 into the interior 50 of the housing 48, with the fasteners 80 disposed on both sides of the window 68. At least one of the emitters 30 of the UVC radiation 32 is positioned to emit the UVC radiation 32 onto the exposed portion 70 of the first primary surface 60 of the wound portion 56 of the seatbelt webbing 26. For example, the attachment portion 74, at the first surface 72, supports at least one emitter 30 to emit the UVC radiation 32 through the window 68 of the housing 48, into the interior 50 of the housing 48, and onto the exposed portion 70 of the first primary surface 60 of the wound portion 56 of the seatbelt webbing 26. As such, at least one emitter 30 is operably coupled to the housing 48, via the emitter support structure 28, to emit the UVC radiation 32 onto the seatbelt webbing 26.

The emitter support structure 28 further includes an extension portion 82 that extends away from the attachment portion 74 and the retractor 44, in the direction of the length 54 of the seatbelt webbing 26. Like the attachment portion 74, the extension portion 82 supports at least one emitter 30 of the UVC radiation 32. More specifically, the first surface 72 of the emitter support structure 28 is contiguous from the attachment portion 74 to the extension portion 82. At the extension portion 82, the emitter support structure 28 supports and positions the emitters 30 of the UVC radiation 32 at the first surface 72 such that the emitters 30 emit the UVC radiation 32 onto the first primary surface 60 of the seatbelt webbing 26 at the unwound portion 58 of the seatbelt webbing 26.

Figure 6:
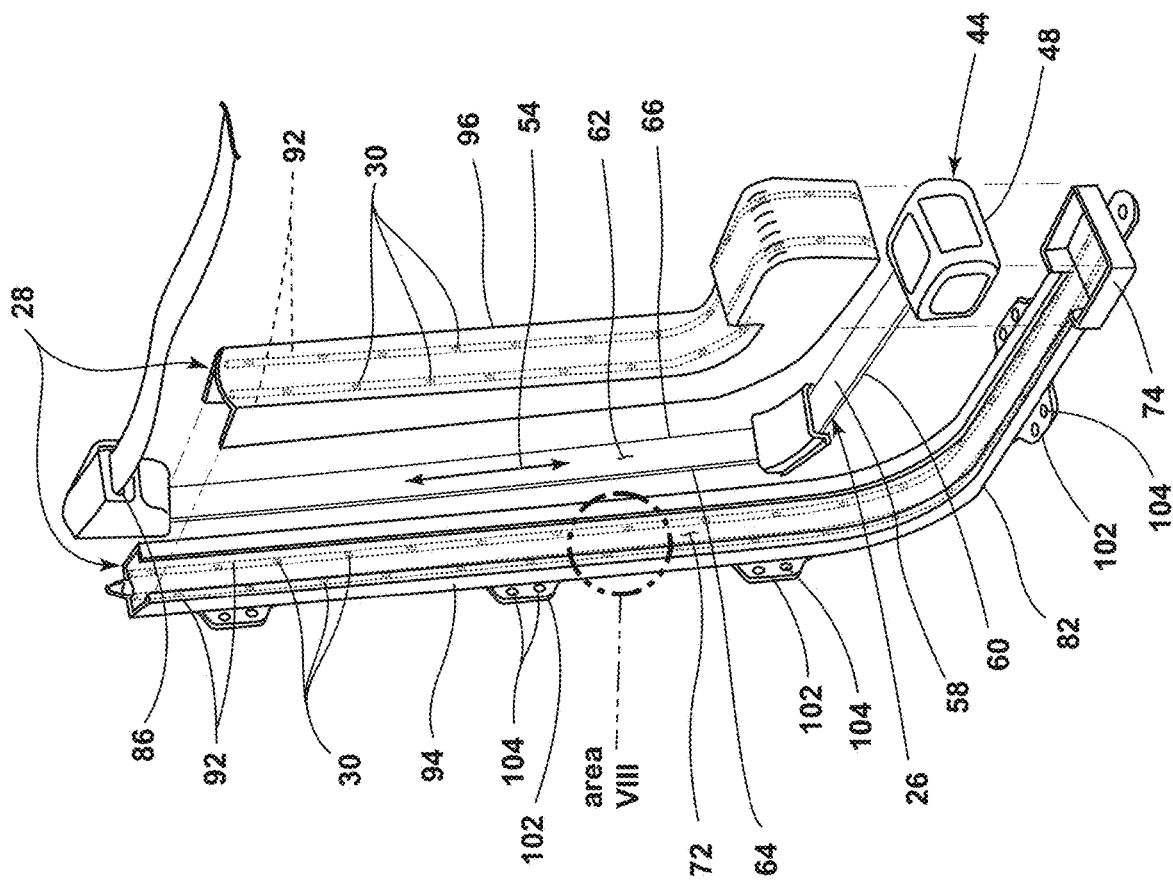
FIG. 6 is an exploded perspective view of the emitter support structure and seatbelt webbing of FIG. 1, illustrating the emitter support structure having a first housing portion and a second housing portion cooperating to enclose the retractor and a portion of the seatbelt webbing extending from the retractor to the top portion of the seatback.

Referring now additionally to FIG. 6, in the illustrated embodiment, the unwound portion 58 extends rearward away from the housing 48 toward the rear side 40 of the seatback 22, and is disposed between the bottom portion 36 of the seat 20 and the floor portion 16. The unwound portion 58 of the seatbelt webbing 26 then extends upwards generally parallel to the rear side 40 of the seatback 22 and adjacent to (just rearward of) the rear side 40 of the seatback 22 toward the top portion 42 of the seatback 22. The unwound portion 58 of the seatbelt webbing 26 then extends from the top portion 42 of the seatback 22 at least partially downwards and generally parallel to the occupant side 38 of the seatback 22. The emitter support structure 28 supports and positions the emitters 30 adjacent to the first primary surface 60 of the seatbelt webbing 26 to emit the UVC radiation 32 onto the first primary surface 60 of the seatbelt webbing 26 along at least a portion of the unwound portion 58 of the seatbelt webbing 26 that extends from the retractor 44 and then along the rear side 40 of the seatback 22. In the illustrated embodiment, the emitter support structure 28 supports and positions the emitters 30 adjacent to the first primary surface 60 along the entire portion of the unwound portion 58 that extends from the retractor 44 to the top portion 42 of the seatback 22.

Figure 7:
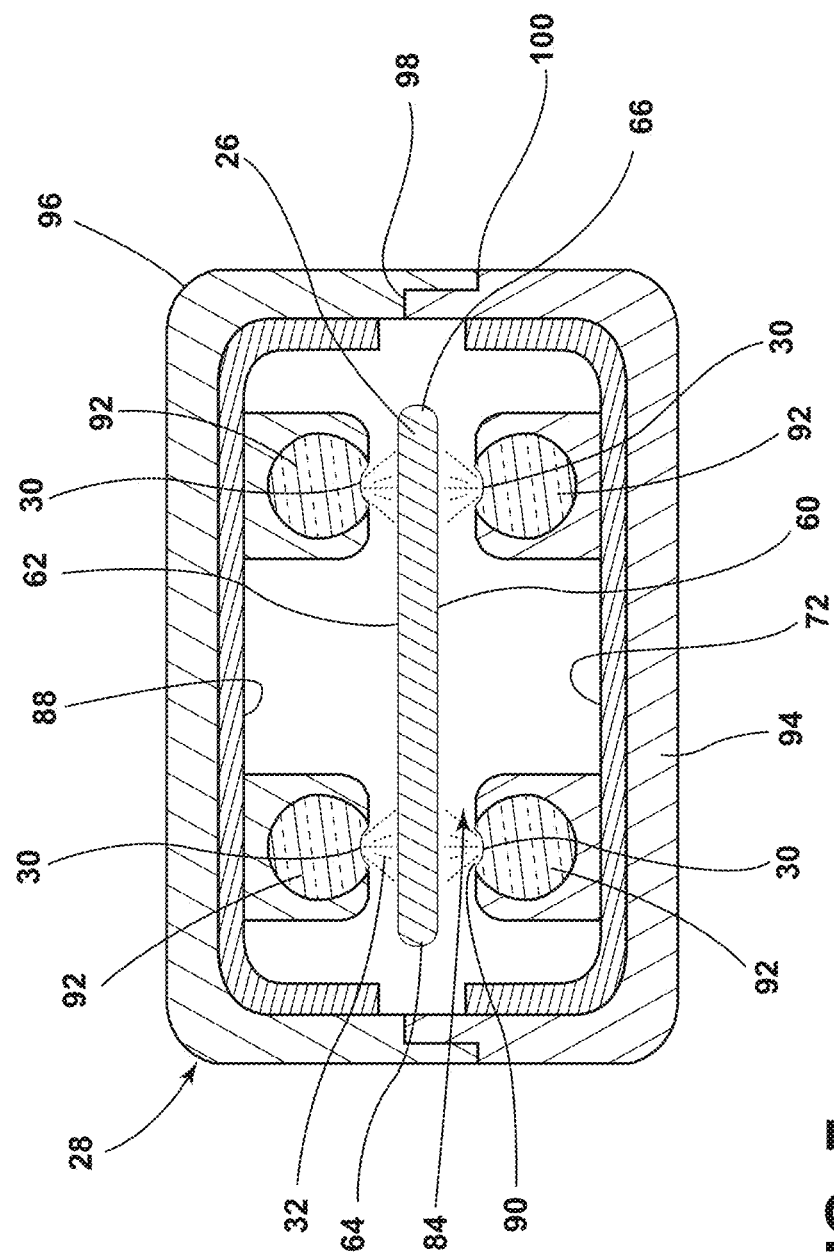
FIG. 7 is an elevational view of the cross-section taken along line VII-VII of FIG. 4, illustrating the first housing portion and the second housing portion of the emitter support structure forming a chamber through which a portion of the unwound portion of the seatbelt webbing extends and can move, and the first housing portion and the second housing portion each support emitters of UVC radiation to emit UVC radiation onto the seatbelt webbing within the chamber to disinfect the seatbelt webbing.

Referring now additionally to FIG. 7, the emitter support structure 28 forms a chamber 84 and structurally supports the plurality of emitters 30 to emit the UVC radiation 32 within the chamber 84. The chamber 84 surrounds the unwound portion 58 of the seatbelt webbing 26 that extends from the retractor 44, upwards alongside and generally parallel to the rear side 40 of the seatback 22, terminating at an outlet 86 that is disposed at or near the top portion 42 of the seatback 22. As will be discussed further below, the chamber 84 permits the unwound portion 58 of the seatbelt webbing 26 to slide through the chamber 84.

In addition to the first surface 72, the emitter support structure 28 further includes a second surface 88. The first surface 72 and the second surface 88 define at least a portion of the chamber 84. The second surface 88 faces the second primary surface 62 of the seatbelt webbing 26. The first surface 72 and the second surface 88 generally face toward each other. In some embodiments, the first surface 72 and the second surface 88 are contiguous. The emitter support structure 28 supports and positions the emitters 30 of the UVC radiation 32 between the second primary surface 62 of the seatbelt webbing 26 and the second surface 88 of the emitter support structure 28 such that the UVC radiation 32 is emitted along at least a portion of the unwound portion 58 of the seatbelt webbing 26 that extends from the retractor 44 and then along the rear side 40 of the seatback 22. In the illustrated embodiment, the emitter support structure 28 supports and positions the emitters 30 to emit the UVC radiation 32 onto the second primary surface 62 of the seatbelt webbing 26 along the entirety of unwound portion 58 of the seatbelt webbing 26 that extends from the retractor 44 to the top portion 42 of the seatback 22.

Figure 8:
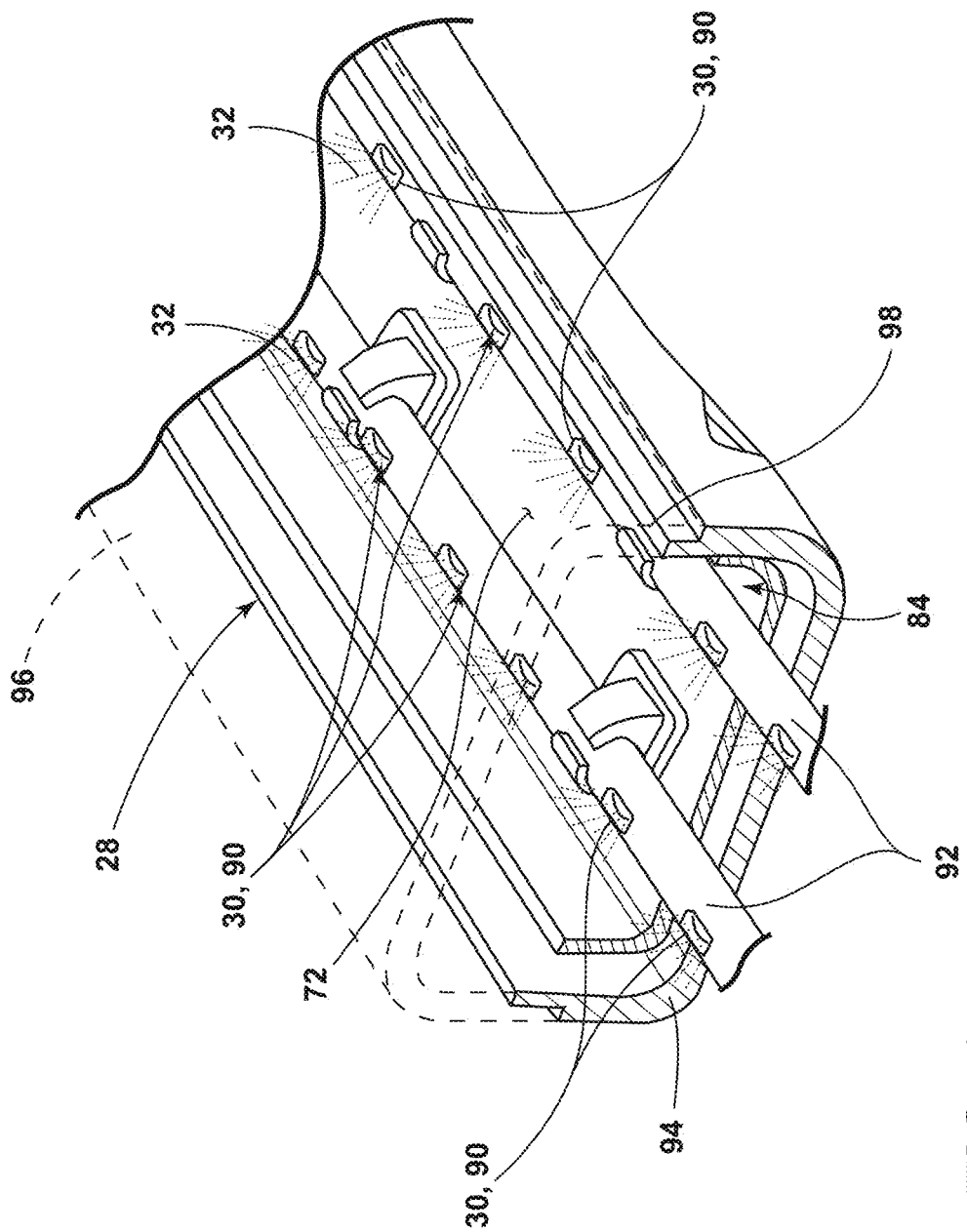
FIG. 8 is a perspective view of area VIII of FIG. 6, illustrating the first housing portion of the emitter support structure supporting light pipes having cutouts, and the light pipes transmit UVC radiation that exits through the cutouts.

Referring now additionally to FIG. 8, in the illustrated embodiment, each of the emitters 30 of the UVC radiation 32 is a cutout 90 (such as a pyramidal or an ovoid cutout) into one or more light pipes 92. The light pipes 92 transmit the UVC radiation 32 from a source of the UVC radiation 32 (not illustrated) throughout the light pipes 92 via internal reflection. The cutouts 90 interrupt the internal reflection of the UVC radiation 32 and the UVC radiation 32 emits from the light pipe 92 out of the light pipe 92 through each of the cutouts 90. The UVC radiation 32 transmits through the light pipe 92, through the cutouts 90, and onto the seatbelt webbing 26. Each of the first surface 72 and the second surface 88 can support one light pipe 92, two light pipes 92, or any number of the light pipes 92. Instead of the light pipes 92 with the cutouts 90, the emitters 30 of the UVC radiation 32 can be UVC light emitting diodes (LEDs), as further discussed below. A light pipe is sometimes referred to as a light guide.

The first surface 72 and the second surface 88 of the emitter support structure 28 can reflect the emitted UVC radiation 32, to increase the surface area of the seatbelt webbing 26 upon which the UVC radiation 32 impinges. Examples of materials that reflect the UVC radiation 32 and thus can be used to provide the first surface 72 and the second surface 88 include biaxially-oriented polyethylene terephthalate polyester film (tradename Mylar) and metal foils. The entirety of surfaces of the emitter support structure 28 defining the chamber 84 can be UVC radiation 32 reflective, to increase the efficiency of the impingement of the UVC radiation 32 onto the seatbelt webbing 26 (and thus increase germicidal efficacy) and to prevent the remainder of the emitter support structure 28 from degrading upon interaction with the UVC radiation 32.

Referring back to FIGS. 2, 3, and 6, the emitter support structure 28 of the illustrated embodiment includes a first housing portion 94 and a second housing portion 96. The first housing portion 94 and the second housing portion 96 each include an edge portion 98, 100 respectively, that cooperate to allow the first housing portion 94 and the second housing portion 96 to nest together and thus form the chamber 84. The first housing portion 94 includes attachment flanges 102 that extend laterally and include apertures 104 to receive fasteners (not illustrated), that permit the emitter support structure 28 to become fastened to the seating assembly 14a. Fasteners (not illustrated) are placed through the apertures 104 of the first housing portion 94 and into fastener receivers (not illustrated) disposed in the seatback 22 at the rear side 40 thereof and in the seat 20. Because the second housing portion 96 is nested with the first housing portion 94 and disposed between the first housing portion 94 and the seatback 22 or the seat 20, the fastening of the first housing portion 94 of the emitter support structure 28 to the seatback 22 or the seat 20, depending on location, traps the second housing portion 96 in place.

To prevent or minimize the leaking of the UVC radiation 32 out of the chamber 84 and into the interior 12 of the vehicle 10, the first housing portion 94 and the second housing portion 96 cooperate to encase the retractor 44, except for any support structure connecting the retractor 44 to the frame 46 of the seat 20. Following the unwound portion 58 of the seatbelt webbing 26 extending from the retractor 44, the first housing portion 94 and the second housing portion 96 together form the chamber 84 that extends lengthwise along and surrounds the unwound portion 58 of the length 54 of the seatbelt webbing 26 from the retractor 44 to the outlet 86. The chamber 84 extends continuously from the retractor 44, along the rear side 40 of the seatback 22, and terminates at or near the top portion 42 of the seatback 22 at the outlet 86. The UVC radiation 32 that is emitted within the chamber 84 thus stays within the chamber 84 and is prevented from leaking out of the emitter support structure 28 except perhaps at the outlet 86. Leak of the UVC radiation 32 at the outlet 86 can be minimized by minimizing the size of the outlet 86 to approximately the width (between the first edge 64 and the second edge 66) and thickness (between the first primary surface 60 and the second primary surface 62) of the seatbelt webbing 26 extending through the outlet 86.

Figure 9:
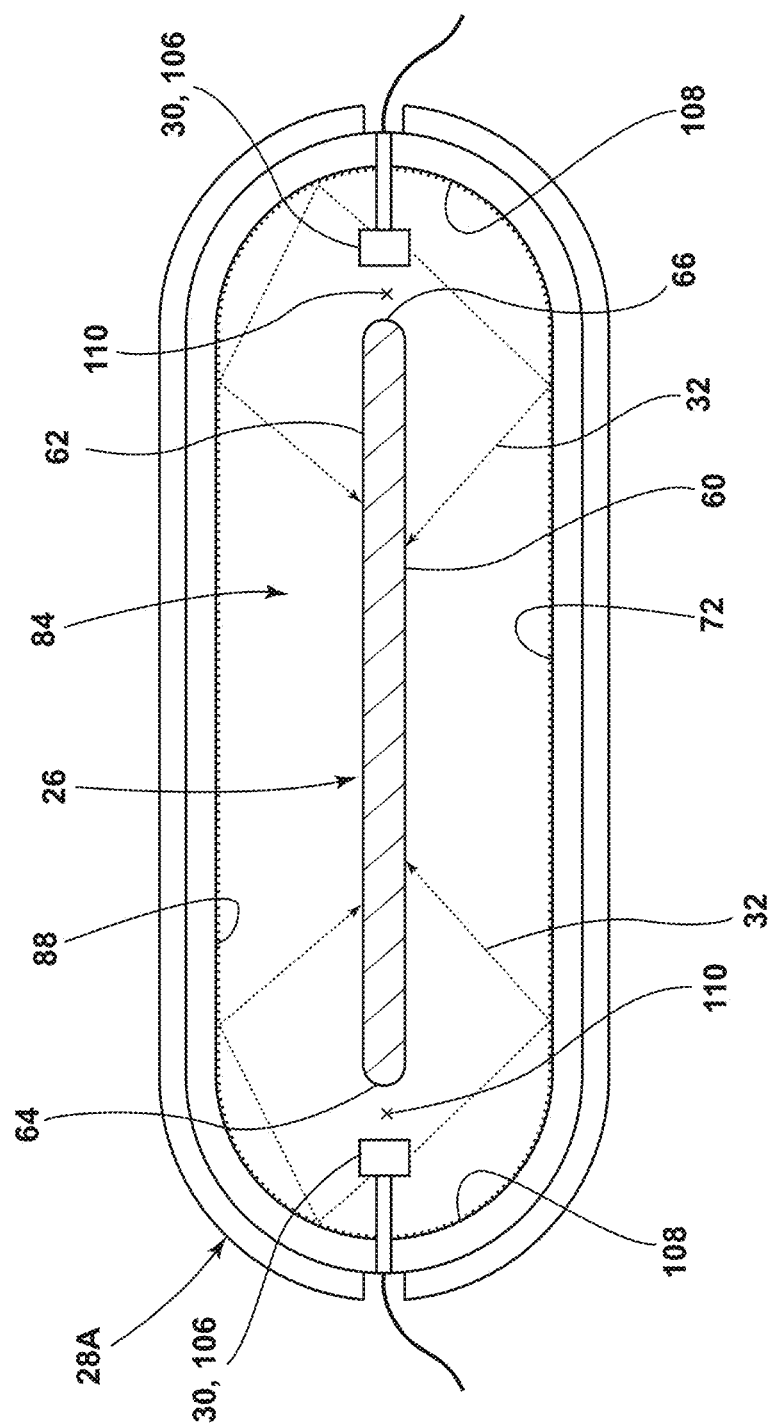
FIG. 9 is an elevational view of a cross-section like FIG. 7 but illustrating an alternative embodiment emitter support structure that supports UVC light emitting diodes (LEDs) as the emitters of UVC radiation, and the UVC LEDs are positioned adjacent edges of the seatbelt webbing and cooperate with parabolic reflective surfaces to emit UVC radiation onto the seatbelt webbing.

Referring now to FIG. 9, an alternative embodiment emitter support structure 28A supports the emitters 30 of the UVC radiation 32 adjacent to the first edge 64 and the second edge 66 of the unwound portion 58 of the seatbelt webbing 26. In other embodiments, the emitters 30 of the UVC radiation 32 can be adjacent to either the first edge 64 or the second edge 66. Instead of the light pipes 92, the emitters 30 of the UVC radiation 32 can be individual LEDs 106 that emit the UVC radiation 32, as illustrated with this embodiment of the emitter support structure 28A. The emitter support structure 28A again forms the chamber 84 but this time includes a parabolic reflective surface 108 cooperating with each of the emitters 30 and disposed opposing one of the first edge 64 or the second edge 66 of the seatbelt webbing 26 as the case may be. Each parabolic reflective surface 108 has a focal point 110, respectively. If the LED 106 or other emitter 30 of the UVC radiation 32 is positioned at the focal point 110, the emitted UVC radiation 32 is emitted as parallel beams, which may result in suboptimal impingement of the UVC radiation 32 onto the first primary surface 60 and the second primary surface 62 of the seatbelt webbing 26. However, if the LED 106 or other emitter 30 is positioned between the parabolic reflective surface 108 and the focal point 110, as in the illustrated embodiment, then the emitted UVC radiation 32 forms diverging light beams as illustrated. The diverging light beams have a higher chance of impinging the first primary surface 60 and the second primary surface 62 of the seatbelt webbing 26 than the parallel beams.

Figure 10:
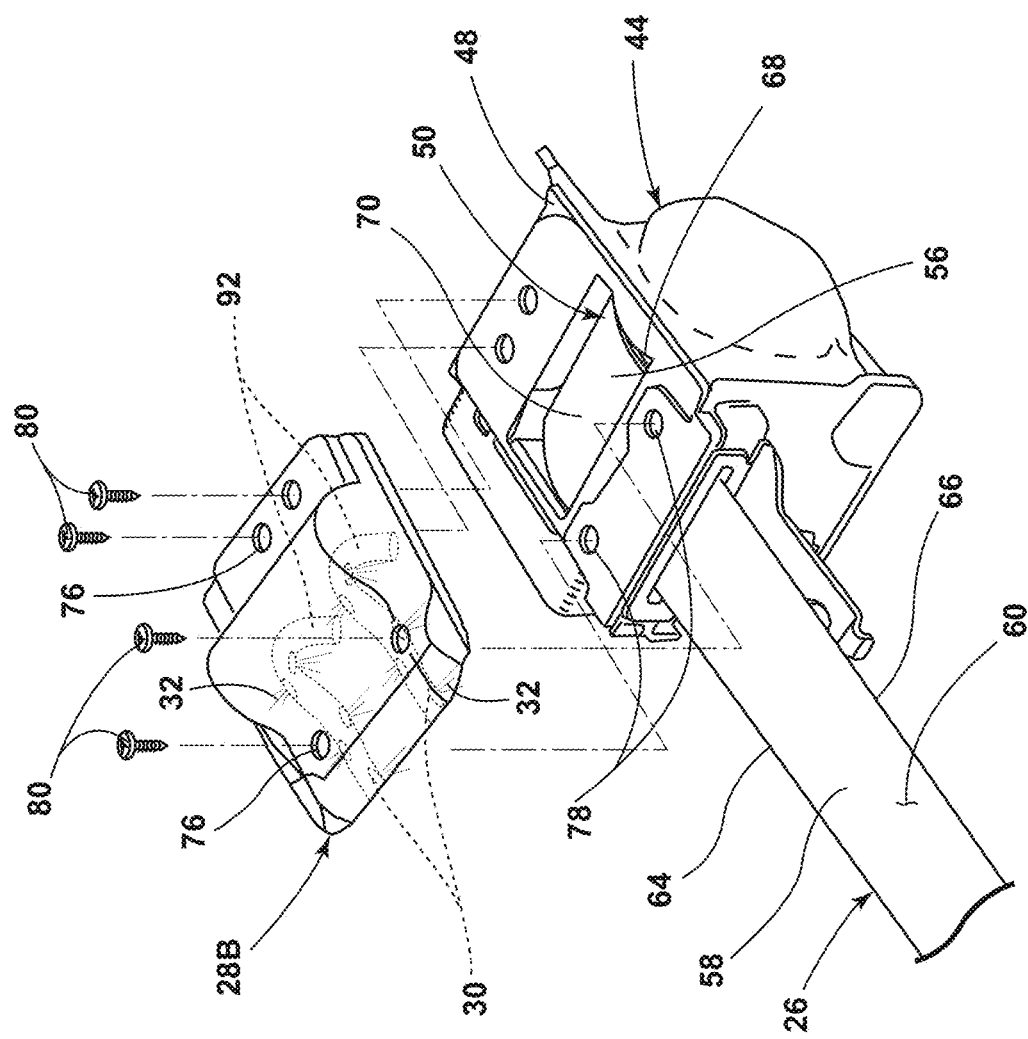
FIG. 10 is an underside perspective view like FIG. 4, but illustrating, in exploded view, an alternative embodiment emitter support structure that is only attached to a housing of the retractor such that emitters of UVC radiation are positioned to emit UVC radiation onto an exposed portion of a wound portion of the seatbelt webbing through a window in the housing of the retractor.

Referring finally to FIG. 10, an alternative embodiment emitter support structure 28B resembles a cap and is limited to covering the window 68 into the interior 50 of the housing 48 of the retractor 44. The emitter support structure 28B still supports one or more of the emitters 30 of the UVC radiation 32. However, the emitted UVC radiation 32 impinges upon only the wound portion 56 of the length 54 of the seatbelt webbing 26 that sits within the interior 50 of the housing 48. Among other things, the alternative embodiment emitter support structure 28B serves to demonstrate that the emitter support structure 28B can support any number of the emitters 30 to impinge any portion of the length 54 of the seatbelt webbing 26 with the UVC radiation 32, from only the wound portion 56 within the housing 48 of the retractor 44, to all of the length 54 of the seatbelt webbing 26 from and including the retractor 44 to the outlet 86, which may be situated at the top portion 42 of the seatback 22, to any portion of the length 54 in between. In some embodiments, the chamber 84 that the emitter support structure 28B forms extends only along the rear side 40 of the seatback 22, from the outlet 86 at the top portion 42 of the seatback 22 to the bottom portion 36 of the seat 20, without curving under the seat 20 and over the floor portion 16.

Figure 11:
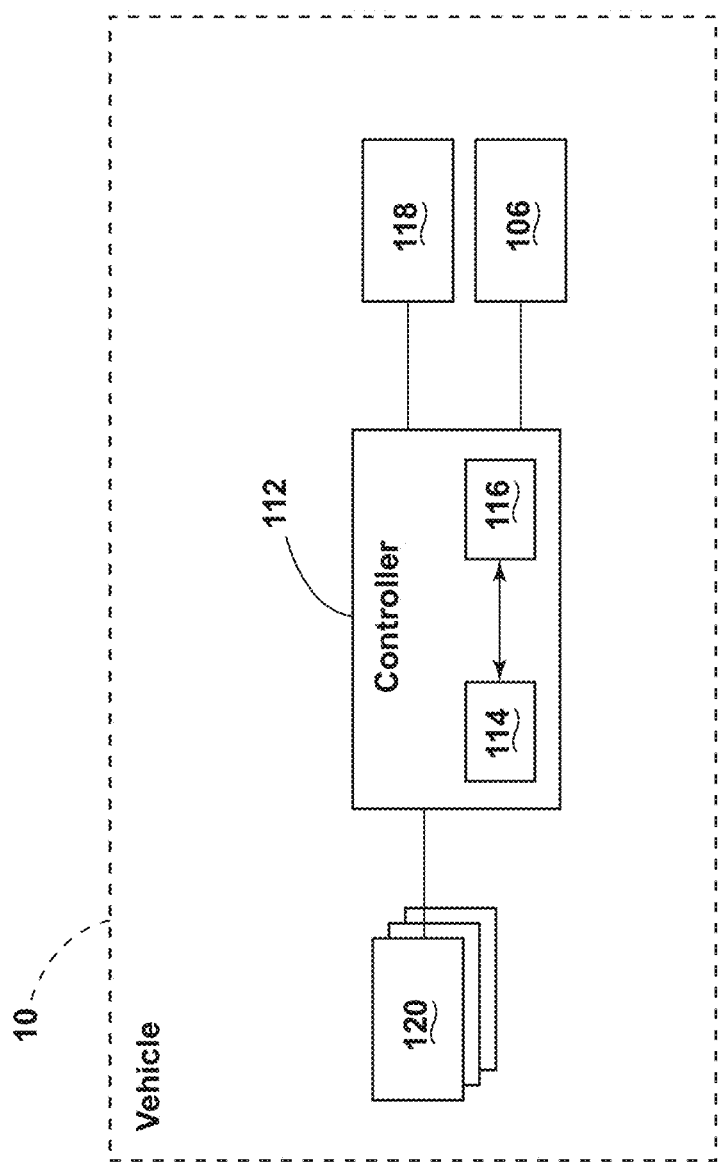
FIG. 11 is a schematic diagram of a controller of the vehicle of FIG. 1, illustrating that the controller controls the UVC LEDs and/or UVC radiation source from which the emitters of UVC radiation obtain the UVC radiation, as a function of input data provided by various sensors within the vehicle.

Referring now to FIG. 11, the vehicle 10 further includes a controller 112. The controller 112 includes a microprocessor 114 and a memory 116. The memory 116 stores programs that the microprocessor 114 executes, and data that the microprocessor 114 during execution of the programs. The controller 112 is in communication with and controls the activation and deactivation of a UVC radiation source 118 that supplies the one or more light pipes 92 (and thus the emitters 30) with UVC radiation and/or the UVC LEDs 106. On the input side, the controller 112 is in communication with, whether directly or indirectly, various other sensor(s) 120 that provide data regarding various vehicle 10 states. For example, the various other sensor(s) 120 can include a sensor that provides data as to whether a passenger door (not illustrated) has opened, a sensor that provides data as to whether the occupant 18 is or is not occupying the seating assembly 14a, a sensor that provides data as to whether a "remote start" feature has caused an engine of the vehicle 10 to begin operating.

In use, the controller 112 can cause the UVC radiation source 118 and/or the UVC LEDs 106 to produce UVC radiation (and thus the emitters 30 to emit UVC radiation) onto the seatbelt webbing 26 as a function of the input data from the various other sensor(s) 120.

In some instances, the controller 112 causes the UVC radiation source 118 and/or the UVC LEDs 106 to emit UVC radiation onto the seatbelt webbing 26 upon receiving input data from the various other sensor(s) 120 that indicate that the seatbelt webbing 26 is about to be utilized, in order to treat the seatbelt webbing 26 just prior to use. In an embodiment, when the various other sensor(s) 120 generate input data to the controller 112 that the "remote start" feature has caused an engine of the vehicle 10 to begin operating, the controller 112 causes the UVC radiation source 118 and/or the UVC LEDs 106 to emit UVC radiation onto the seatbelt webbing 26. In an embodiment, when the various other sensor(s) 120 generate input data to the controller 112 that the door handle of the door nearest the seating assembly 14a has been touched, the controller 112 causes the UVC radiation source 118 and/or the UVC LEDs 106 to emit UVC radiation onto the seatbelt webbing 26. In another embodiment, when the various other sensor(s) 120 generate input data to the controller 112 that the passenger door nearest the seating assembly 14*a* has opened, the controller 112 causes the UVC radiation source 118 and/or the UVC LEDs 106 to emit UVC radiation onto the seatbelt webbing 26. In another embodiment, when the various other sensor(s) 120 generate input data to the controller 112 that the seating assembly 14*a* has become occupied, the controller 112 causes the UVC radiation source 118 and/or the UVC LEDs 106 to emit UVC radiation onto the seatbelt webbing 26.

In other instances, the controller 112 causes the UVC radiation source 118 and/or the UVC LEDs 106 to emit UVC radiation onto the seatbelt webbing 26 upon receiving input data from the various other sensor(s) 120 that indicate that the seatbelt webbing 26 is no longer being utilized, in order to treat the seatbelt webbing 26 before the next use thereof. In an embodiment, when the various other sensor(s) 120 generate input data to the controller 112 that the occupant 18 was, but is no longer, occupying the seating assembly 14*a*, the controller causes the UVC radiation source 118 and/or the UVC LEDs 106 to emit UVC radiation onto the seatbelt webbing 26. When the occupant 18 thereafter occupies the seating assembly 14*a* and extracts the seatbelt webbing 26 to place the seatbelt webbing 26 over the occupant 18 to secure the occupant 18 to the seating assembly 14*a*, at least a portion of the length 54 of the seatbelt webbing 26 that contacts the occupant 18 is in a disinfected state and does not harbor potentially harmful microorganisms.

After a predetermined amount of time sufficient to produce germicidal effects, such as a few seconds, the controller 112 causes the UVC radiation source 118 and/or the UVC LEDs 106 to no longer emit UVC radiation onto the seatbelt webbing 26.

In some embodiments, the various other sensor(s) 120 include a sensor 120 localized to the retractor 44, to provide input data that the seatbelt webbing 26 is retracting into or out of the retractor 44. In an embodiment, the controller 112 causes the UVC radiation source 118 and/or the UVC LEDs 106 to emit UVC radiation onto the seatbelt webbing 26 upon receiving input data that the seatbelt webbing 26 is retracting into the retractor 44. In an embodiment, the controller 112 causes the UVC radiation source 118 and/or the UVC LEDs 106 to emit UVC radiation onto the seatbelt webbing 26 upon receiving input data that the seatbelt webbing 26 is extracting out of the retractor 44. In an embodiment, the controller 112 causes the UVC radiation source 118 and/or the UVC LEDs 106 to emit UVC radiation onto the seatbelt webbing 26 upon receiving input data that the seatbelt webbing 26 is either extracting out of the retractor 44, or retracting into the retractor 44.

Figure 12:
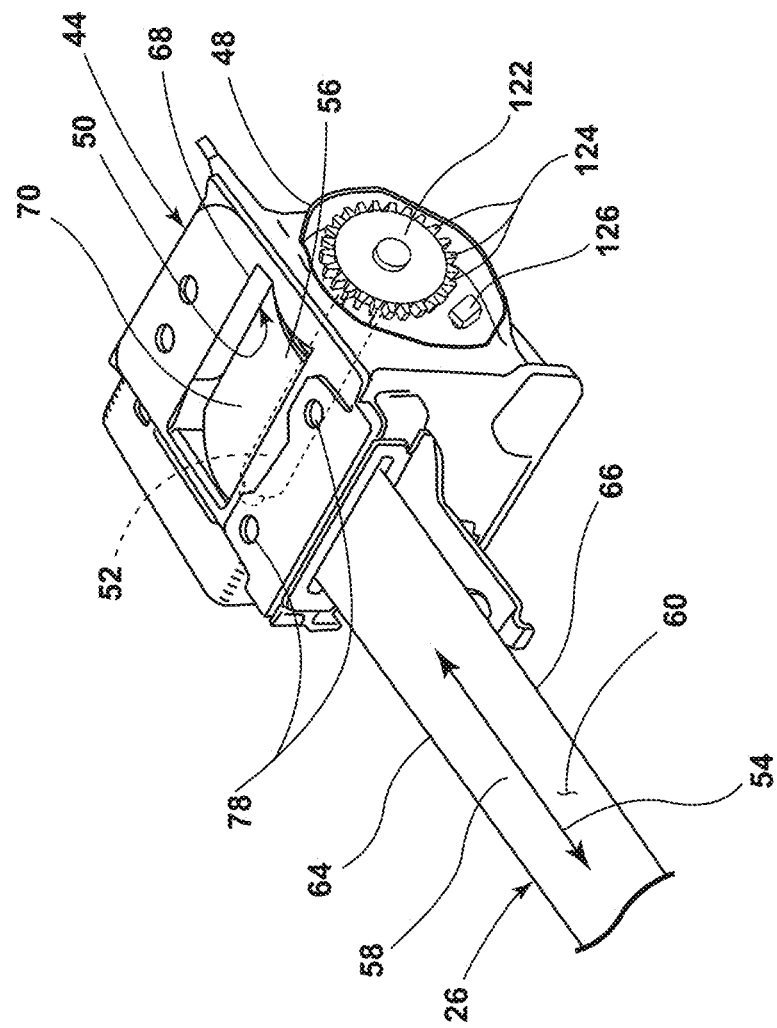
FIG. 12 is a perspective view of an embodiment of the retractor that includes one such sensor that provides input data to the controller, illustrating that the sensor includes a rotor attached to the shaft of the retractor, the rotor having magnetic teeth that interact with a magnetic sensor upon rotation of the rotor due to retraction or extraction of the seatbelt webbing.

Referring now to FIG. 12, this sensor 120 localized to the retractor 44 can be a magnetic interaction sensor that utilizes a rotor 122 with teeth 124, which are magnetic, and a magnetic detection device 126. The rotor 122 is attached to the shaft 52 or some other rotating element of the retractor 44 that rotates when the seatbelt webbing 26 is extracted or retracted. As the rotor 122 rotates, the magnetic teeth 124 magnetically interact with the magnetic detection device 126. The magnetic detection device 126 can be a Hall effect sensor, or an inductive sensor.

Figure 13A:
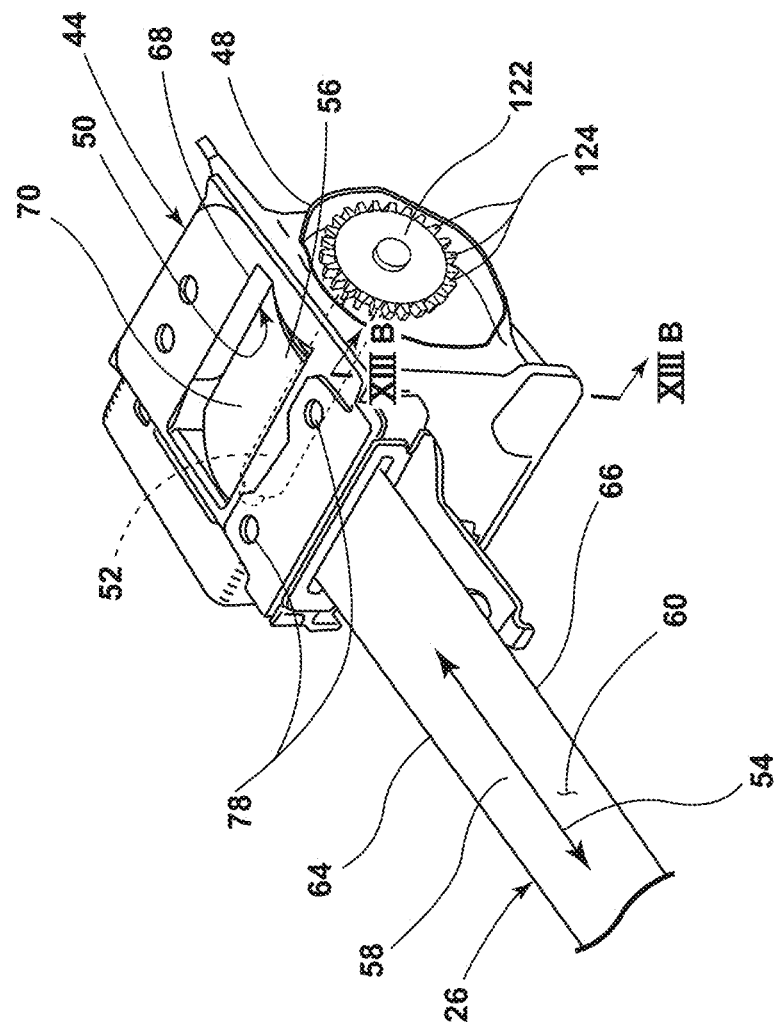
FIGS. 13A and 13B is a perspective view, and a cross-sectional view of FIG. 13A taken through line XIIIB-XIIIB respectively, of an embodiment of the retractor that includes one such sensor that provides input data to the controller, illustrating that the sensor includes a rotor attached to the shaft of the retractor, the rotor having teeth that interact with an LED and light sensor upon rotation of the rotor due to retraction or extraction of the seatbelt webbing.
Figure 13B:
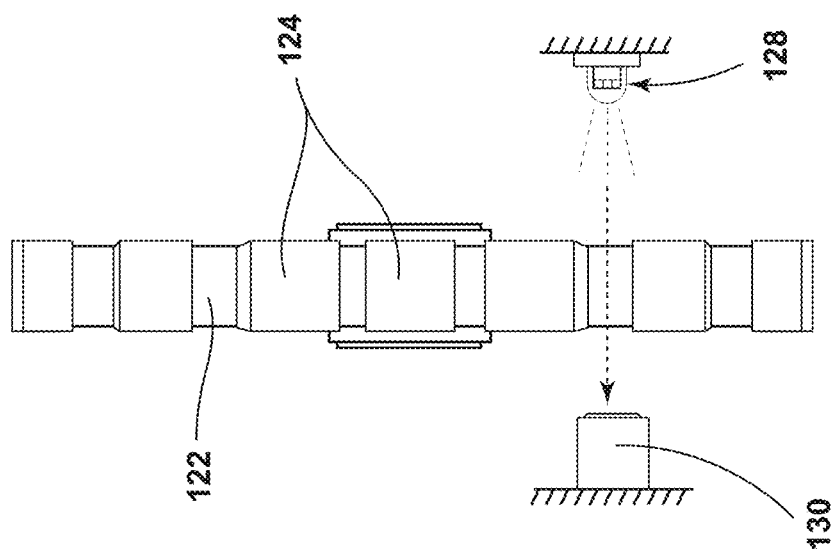

Referring now to FIGS. 13A and 13B, this sensor 120 localized to the retractor 44 can be a light-based sensor that again utilizes the rotor 122 with teeth 124, an LED 128, and a light sensor 130. In the illustrated embodiment, the output of the light sensor 130 changes as a function of the amount of light received from the LED 128. As the rotor 122 rotates, the teeth 124 interrupt the path of light from the LED 128 to the light sensor 130 thus creating a variation in the output of the light sensor 130. In the illustrated embodiment, the light sensor 130 is disposed on the opposite side of the rotor 122 as the LED 128. However, in another embodiment, the retractor 44 is reflective of the light of the LED 128 and thus the light sensor 130 can be disposed adjacent to the LED 128. The light sensor 130 and the LED 128 are positioned such that when a tooth 124 is in a reflective light path between the light sensor 130 and the LED 128, the light sensor 130 receives the reflected light. When the tooth 124 is not in a reflective light path, the light sensor 130 does not receive the reflected light. Thus, as the rotor 122 rotates, the teeth 124 alternate being in the reflective light path and not being in the reflective light path, thus varying the output of the light sensor 130 indicating rotation of the rotor 122 and thus retraction or extraction of the seatbelt webbing 26.

Each of these sensors 120 localized to the retractor 44 can provide output data in the form of a pulse train (such as voltage). From the pulse train, the speed and distance of the retraction/extraction of the seatbelt webbing 26 can be calculated, should such calculations be necessary. Duplicative magnetic sensors or light sensors, as the case may be, can be utilized to provide data concerning direction of rotation of the rotor 122 to indicate extraction or retraction of the seatbelt webbing 26. Other mechanical sensors are of course possible to indicate extraction or retraction of the seatbelt webbing 26.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the afore-mentioned structure without departure from the concepts of the present disclosure, and further it is to be understood that such concepts are intended to be covered by the following claims unless these claims by their language expressly state otherwise.

What is claimed is:

1. A vehicle comprising:
    seatbelt webbing, the seatbelt webbing including a length, which includes a wound portion and an unwound portion;
    a retractor, the retractor including a housing supporting a shaft, around which the wound portion of the length of the seatbelt webbing is wound, wherein the unwound portion of the seatbelt webbing extends away from the housing; and
    one or more emitters of ultraviolet C ("UVC") radiation operably coupled to the housing of the retractor and positioned to emit the UVC radiation onto the seatbelt webbing.

2. The vehicle of claim 1, wherein
    the seatbelt webbing further includes a first primary surface, a second primary surface that faces in an opposite direction as the first primary surface, a first edge, and a second edge, the first primary surface and the second primary surface extending laterally from the first edge to the second edge and lengthwise along the length of the seatbelt webbing;
    at least an exposed portion of the first primary surface of the wound portion of the seatbelt webbing is exposed within the housing; and
    the one or more emitters of the UVC radiation is positioned to emit the UVC radiation onto the exposed portion of the first primary surface of the wound portion of the seatbelt webbing.

3. The vehicle of claim 2 further comprising:
an emitter support structure including:
  an attachment portion attached to the housing of the retractor, the attachment portion supporting at least one of the emitters of the UVC radiation to emit the UVC radiation onto the exposed portion of the first primary surface of the wound portion of the seatbelt webbing; and
  an extension portion extending away from the attachment portion and the retractor, the extension portion supporting at least one other of the emitters of the UVC radiation to emit the UVC radiation onto the first primary surface of the seatbelt webbing at the unwound portion of the seatbelt webbing.

4. The vehicle of claim 1 further comprising:
an emitter support structure that operably couples the one or more emitters of the UVC radiation to the housing of the retractor, the emitter support structure comprises a first surface facing a first primary surface of the seatbelt webbing, the emitter support structure supporting the one or more emitters of the UVC radiation between the first primary surface of the seatbelt webbing and the first surface of the emitter support structure.

5. The vehicle of claim 4, wherein
the emitter support structure supports the one or more emitters of the UVC radiation between the first primary surface of the seatbelt webbing and the first surface of the emitter support structure such that the UVC radiation is emitted along at least a portion of the unwound portion of the length of the seatbelt webbing.

6. The vehicle of claim 5, wherein
the emitter support structure further includes a second surface facing a second primary surface of the seatbelt webbing that faces in an opposite direction as the first primary surface of the seatbelt webbing, and
the emitter support structure supports at least one of the emitters of the UVC radiation between the second primary surface of the seatbelt webbing and the second surface of the emitter support structure.

7. The vehicle of claim 1, wherein
the one or more emitters of the UVC radiation include a cutout into a light pipe, which transmits the UVC radiation, such that the UVC radiation transmits through the light pipe, through the cutout and onto the seatbelt webbing.

8. The vehicle of claim 4, wherein
the first surface of the emitter support structure reflects the UVC radiation.

9. The vehicle of claim 4, wherein
the emitter support structure surrounds at least a portion of the unwound portion of the length of the seatbelt webbing.

10. The vehicle of claim 4, wherein
the emitter support structure further comprises a first housing portion providing the first surface of the emitter support structure and a second housing portion coupled to the first housing portion; and
the first housing portion and the second housing portion of the emitter support structure form a chamber that houses at least a portion of the unwound portion of the length of the seatbelt webbing, and at least one of the one or more emitters of the UVC radiation is positioned to emit the UVC radiation into the chamber.

11. The vehicle of claim 1 further comprising:
a floor portion;
a seating assembly including:
  a seat including a bottom portion that generally faces the floor portion, and
  a seatback including an occupant side that is configured to contact and support an occupant of the seating assembly, a rear side that generally faces rearward from the perspective of the occupant, and a top portion that is furthest away from the floor portion of the vehicle;
wherein, the retractor is disposed between the floor portion of the vehicle and the bottom portion of the seat;
wherein, the unwound portion of the seatbelt webbing extends rearward away from the housing, then upwards generally parallel to the rear side of the seatback, then over the top portion of the seatback, and then at least partially downwards generally parallel to the forward side of the seatback; and
the one or more emitters of the UVC radiation include a plurality of emitters of the UVC radiation adjacent the seatbelt webbing to emit the UVC radiation onto the seatbelt webbing where the unwound portion of the seatbelt webbing extends upwards generally parallel to the rear side of the seatback.

12. The vehicle of claim 11 further comprising:
an emitter support structure that forms a chamber that surrounds the unwound portion of the seatbelt webbing that extends upwards generally parallel to the rear side of the seatback and structurally supports the plurality of emitters of the UVC radiation within the chamber.

13. The vehicle of claim 12, wherein
the seatbelt webbing further includes a first primary surface, a second primary surface that faces in an opposite direction as the first primary surface, a first edge, and a second edge, the first primary surface and the second primary surface extending laterally from the first edge to the second edge and lengthwise along the length of the seatbelt webbing; and
the plurality of emitters of the UVC radiation are positioned to emit the UVC radiation onto both the first primary surface and the second primary surface of the seatbelt webbing.

14. The vehicle of claim 13, wherein
the emitter support structure includes a parabolic reflective surface cooperating with each of the plurality of emitters of the UVC radiation and disposed opposing the first edge or the second edge, or both, of the seatbelt webbing, each parabolic reflective surface having a focal point, and each of the plurality of emitters of the UVC radiation is positioned between the parabolic reflective surface and the focal point.

15. The vehicle of claim 13, wherein
the emitter support structure includes a first surface facing the first primary surface of the seatbelt webbing, and a second surface facing the secondary primary surface of the seatbelt webbing;
the emitter support structure supports at least one of the plurality of emitters of the UVC radiation between the first primary surface of the seatbelt webbing and the first surface of the emitter support structure; and
the emitter support structure further supports at least one of the plurality of emitters of the UVC radiation between the second primary surface of the seatbelt webbing the second surface of the emitter support structure.

16. A seating assembly for a vehicle comprising:
a seat;
a seatback including an occupant side configured to contact and support an occupant of the seating assembly, a rear side that faces in the generally opposite direction as the occupant side, and a top portion;
seatbelt webbing, the seatbelt webbing extending along the rear side of the seatback;
a plurality of emitters of UVC radiation; and
an emitter support structure attached to the seatback that supports the plurality of emitters of the UVC radiation such that the plurality of emitters of the UVC radiation emit the UVC radiation onto the seatbelt webbing extending along the rear side of the seatback.

17. The seating assembly of claim 16,
the emitter support structure forming a chamber that surrounds at least a portion of the seatbelt webbing but allows the seatbelt webbing to move through the chamber, the emitter support structure supporting the plurality of emitters of the UVC radiation to emit the UVC radiation within the chamber.

18. The seating assembly of claim 17 further comprising:
a frame providing structural support for the seat; and
a retractor attached to the frame, the seatbelt webbing able to retract into and extract out of the retractor;
wherein, the seatbelt webbing extends from the retractor then along the rear side of the seatback toward the top portion; and
wherein, the emitter support structure at least partially encases the retractor, and the chamber extends continuously from the retractor, alongside the rear side of the seatback, and terminates at or near the top portion of the seatback.

19. An emitter support structure for a seating assembly of a vehicle comprising:
a housing comprising (i) a first housing portion and a second housing portion forming a chamber and (ii) fastening features configured to permit fastening of the emitter support structure to the seating assembly, wherein the first housing portion provides a first surface, the second housing portion provides a second surface, and the first surface and the second surface face each other and define at least a portion of the chamber; and
a plurality of emitters of UVC radiation supported by the housing and -positioned to emit the UVC radiation into the chamber, wherein the first housing portion and the second housing portion each support emitters of the plurality of emitters of the UVC radiation.

20. The emitter support structure of claim 19 further comprising:
a light pipe, and the plurality of emitters of the UVC radiation comprise cutouts into the light pipe.

* * * * *